United States Patent [19]

Halling et al.

[11] Patent Number: 4,863,860
[45] Date of Patent: Sep. 5, 1989

[54] FAT PROCESSING

[75] Inventors: Peter J. Halling, Northamptonshire; Alasdair R. Macrae, Bedford, both of England

[73] Assignee: Lever Brothers Company, New York, N.Y.

[21] Appl. No.: 37,065

[22] Filed: Apr. 13, 1987

Related U.S. Application Data

[63] Continuation of Ser. No. 785,101, Oct. 7, 1985, abandoned, which is a continuation of Ser. No. 451,203, Dec. 7, 1982, abandoned.

[30] Foreign Application Priority Data

May 7, 1981 [GB] United Kingdom ............... 8113953

[51] Int. Cl.$^4$ .............................................. C12P 7/64
[52] U.S. Cl. .................................... 435/134; 426/33; 435/135; 435/174; 435/176; 435/198; 435/271
[58] Field of Search ............... 435/134, 135, 174, 176, 435/198, 271; 426/33

[56] References Cited

U.S. PATENT DOCUMENTS

| | | | |
|---|---|---|---|
| 4,268,527 | 5/1981 | Matsuo et al. | 426/33 |
| 4,275,081 | 6/1981 | Coleman et al. | 426/33 |
| 4,416,991 | 11/1983 | Matsuo et al. | 426/33 |

FOREIGN PATENT DOCUMENTS

| | | |
|---|---|---|
| 0010903 | 5/1980 | European Pat. Off. |
| 0034065 | 8/1981 | European Pat. Off. |
| 0035883 | 9/1981 | European Pat. Off. |
| 2042579 | 9/1980 | United Kingdom |
| 1577933 | 10/1980 | United Kingdom |

OTHER PUBLICATIONS

Colley, Brit. Chem. Eng. Process Technol., vol. 17(3), pp. 229–233, (CA 77:7817v), 1972.
Klibanon et al., Biotech. & Bioeng., vol. XIX, pp. 1351–1361, 1977.
Butler, Enzyme Microb. Technol., vol. 1, pp. 253–259, 1979.
Potthast et al., Internatl. Symp. Proc., Glasgow, pp. 365–377, Academic Press, Sep. 1974.

Primary Examiner—Robert A. Wax
Attorney, Agent, or Firm—Milton L. Honig

[57] ABSTRACT

Organic compounds susceptible to hydrolysis are prepared by reaction in a water-immiscible organic liquid in contact with an enzyme activated with water to catalyze the reaction and desiccant means to lower the water activity of the dispersion from which the reaction products are recovered. The enzyme may be a lipase to catalyze an interesterification process and the desiccant means may be immersed in the dispersion to remove water in the liquid phase or in the headspace above the dispersion to remove water vapor.

17 Claims, No Drawings

FAT PROCESSING

This is a continuation, application of Ser No. 785,101, filed Oct. 7, 1985, now abandoned, which is a continuation of Ser. No. 451,203, filed Dec. 7, 1982, now abandoned.

This invention relates to organic reactions in non-aqueous media.

Many chemical reactions for the preparation of organic products are catalysed by enzymes which therefore find increasing use for this purpose on an industrial scale. Water is required to activate the enzyme from the inert and desiccated condition in which these materials are stored and marketed, often carried on an inert support such as kieselguhr which is itself highly water-absorbent. The introduction of the activated enzyme, therefore, introduces water into the reaction system to be catalysed by the enzyme. The products of many such organic reactions are however susceptible to hydrolysis and form other products by reaction with water, at the expense of the yield of desired product, by reversing or otherwise changing the course of the reaction. They are therefore conducted in water-immiscible, non-aqueous but not anhydrous, liquid.

The tendency for the hydrolysis reactions to occur is a function of the water activity $A_W$ of the reaction system in which the reaction takes place, rather than the "concentration" of water it contains. In a water-immiscible system with only a limited capacity for absorbing water, $A_W$ may remain substantially at its maximum value $A_W=1$ throughout the reaction, thus promoting the production of excessive amounts of hydrolysis products, despite the low total water content.

The present invention is based on the discovery that after the catalyst is introduced, the water activity of the system may be substantially reduced to minimise hydrolysis while maintaining the catalyst in an active condition. The present invention therefore proposes a process for the preparation of organic compounds susceptible to hydrolysis in which reactants dispersed in a water-immiscible organic liquid contact a water-activated enzyme to catalyse the reaction and desiccant means to lower the water activity of the dispersion and recovering the products therefrom.

The water activity of the activated catalyst before adding to the reaction mixture must be greater than 0.5, preferably than 0.9. The water activity of the total reaction system must be sufficient to permit the catalyst to continue to function well and the desiccant selected accordingly, to reach an $A_W$ giving the desired optimum combination of continued catalyst activity and reduced by-products. This $A_W$ can be achieved by choosing the nature and amount of desiccant in accordance with its known adsorption isotherm, or by controlling the rate at which water is transferred from the gas phase, where this method is adopted, as may be estimated by conventional methods.

The water activity may be decreased in the process of the invention by a desiccant in contact with the vapour phase and the process is then carried out in a closed vessel affording a headspace, in contact with a suitable desiccant through which the gases in the vapour phase are circulated. Water vapour may also be removed by condensation using, for example, a cold insert in the vapour space and reduced pressure may be applied.

Desiccants which may be used include molecular sieves of suitable molecular dimensions to retain water vapour selectively, silica gel, alumina, magnesium sulphate and calcium chloride and these desiccants may also be used in the liquid phase. Others, e.g. sulphuric acid, may only be used in the vapour phase.

An important application of the invention is in the treatment of fats for edible or other purposes, in order to modify their physical characteristics by changing the fatty acid composition of the fat and/or their distribution in the glycerides. The use of enzymes to modify fats in this way, by interesterification with or without added free fatty acid to change the overall composition of the triglycerides of the fat, has been disclosed in our British Patent No. 1,577,933. In particular, fats may be upgraded to contain higher amounts of symmetrical disaturated, 2-oleyl triglycerides which are chiefly responsible for the outstanding melting performance of hard butters. By the improvement provided by the present invention these changes are accompanied with less production of undesirable hydrolysis product, in particular of partial glycerides which profoundly affect the properties of fats. The invention is also suitable for making fats for use in margarine and other emulsion food spreads.

The invention may also be used to improve the quality of natural fats by treatment to re-esterify the free fatty acid and/or partial glycerides which may be present. These impurities are usually produced by natural enzyme action on the fat, either in vivo or after the fat is extracted from its plant or animal source. Since each mole of free fatty acid is liberated with a corresponding equivalent of partial glyceride, the two species may be recombined to triglycerides by treatment in accordance with the invention. While there may already be present lipase enzymes, much is likely to be inactive and additional enzyme must be provided in accordance with the invention.

The process of the invention may be applied to batch or continuous operations and is preferably carried out at a temperature from 10° to 70° C., using an enzyme catalyst activated with from 0.1 to 30% water by weight of the catalyst including the catalyst support which preferably comprises a diatomaceous earth, for example celite or hydroxylapatite, titanium dioxide, alumina or silica. The enzyme catalyst may be used in extracted form or it may be used in cells. It may be a free enzyme, usually watersoluble, or immobilised by binding as described. Enzymes used in the invention may be lipase, esterase, protease, peptidase, amidase, glycosidase or hydratase types.

Lipase enzyme catalysts used to effect changes in the composition of fats in the process of the invention may be selective or non-selective in action. Selective catalysts ae preferentially reactive either towards the 1- and 3- or 2-positions of the glyceride molecule. They may be used in a process in which randomisation is correspondingly required in the 1- and 3-positions only, as in the production of a hard butter. The melting characteristics of these may be improved by augmenting the amount of saturated $C_{16}$ and $C_{18}$ fatty acid residues in the 1,3-positions of the triglycerides of a fat, while leaving unaffected predominantly unsaturated fatty acid residues in the corresponding 2-position. For this purpose a 1,3-selective catalyst is used, e.g. *Rhizopus japonicus* lipase. Such catalysts are less effective in converting diglycerides by re-esterification to triglycerides, since they react only with 1,2(2,3)-diglycerides. There is however a relatively labile equilibrium between the 1:2-(2:3)- and 1:3-isomers, enabling continuous isomerisation to the reactive form as this is converted to the triglyceride by esterification of a 1- or 3-position under the influence of the catalyst. Moreover, 1,3-selective catalysts are preferably used in the invention when no overall isomerisation between triglycerides is required in a natural fat. Some natural fats are already random as regards their 1,3-positions and the effect of a 1,3-selective catalyst will therefore be merely to esterify any free fatty acid present, whether this is added or already present in the native fat, into the 1,3-position of glycerides. Glycerol may be added to combine with free fatty acid present to form partial glycerides where these leave the fat unaffected in the required properties. Non-selective catalysts may be used in the invention where their randomising effect on fatty acid residues in both the 1,3- and 2-positions is immaterial to the properties required. For example, the melting characteristics of lauric fats are little changed by complete randomisation.

The appropriate $A_W$ for individual enzymes varies from one to another. Preferably, for example, *Rh japonicus* lipase may be used below 0.3 and *Asp. niger* lipase below 0.4.

The invention is also applicable to the preparation of other esters, for example of wax esters which are esters of fatty alcohols.

EXAMPLE 1

A mixture of 80 g of palm mid-fraction with 40 g stearic acid dissolved in 288 ml petroleum ether (BP 100° to 120° C.) was selectively interesterified by stirring at 40° C. in a vessel with a headspace of 900 ml, in the presence of 12.5 g lipase-celite catalyst previously wetted with 1.0 ml distilled water and allowed to stand 24 hours beforehand. The catalyst was prepared from *Rhizopus japonicus* lipase 2A ex Nagase and Co. Japan with an activity of 1600 lipase units/gram, in accordance with the method described in Example 2 of British patent specification No. 1,577,933, but using 1 part lipase per 5 parts celite with 20 parts water.

The headspace gases were continuously circulated through a bed of 35 g of ⅛" pellets of molecular sieve type 4A ex BDH at 500 ml/minute to remove water vapour.

After six hours stirring was discontinued, the solvent distilled off and the product recovered and analysed for triglyceride (TG), diglyceride (DG) and free fatty acid (FFA).

The triglyceride was recovered and analysed for fatty acid residues. Water activity of the headspace was calculated from its temperature measurement and the water vapour pressure measured in the headspace by "Hydrolog" apparatus, Model No. WMY270 of Endress & Hauser. Results appear in Table III.

Comparative data was obtained by similar operations to Example 1 above, but without headspace circulation (Control A) and also with no water addition to the catalyst (Control B). The data obtained appear in Table 1, all composition entries in which are by weight %. The Table includes an analysis obtained by calculation assuming 100% interesterification in the 1- and 3-positions. The water activity of Control A remained between 0.84 and 0.89 throughout.

TABLE I

| Species | Feed Composition | Product Composition | | | |
|---|---|---|---|---|---|
| | | Example 1 | Control A Activated Catalyst | Control B Dry Catalyst | Complete interesterification (calculated) |
| TG | 66.0 | 68.2 | 51.3 | 66.1 | |
| FFA | 33.3 | 30.6 | 40.0 | 32.3 | |
| DG | 0.7 | 1.2 | 8.7 | 1.7 | |
| Fatty acyl residues in TG | | | | | |
| 14:0 | 1.0 | 0.6 | 0.7 | 0.9 | 0.6 |
| 16:0 | 57.2 | 35.9 | 35.3 | 56.2 | 34.6 |
| 18:0 | 5.7 | 29.8 | 30.5 | 6.1 | 31.0 |
| 18:1 | 31.7 | 29.3 | 29.2 | 32.1 | 29.6 |
| 18:2 | 4.1 | 3.9 | 3.8 | 4.3 | 4.0 |
| 20:0 | 0.4 | 0.4 | 0.4 | 0.3 | 0.2 |

From Table 1 it is clear that a fatty acid composition, more nearly approximating to the theoretical than Control B, is obtained in Example 1, and with substantially less hydrolysis, in comparison with Control A, evident from the low diglyceride and FFA values.

EXAMPLE 2

Partially hydrolysed palm mid-fraction was re-esterified using a lipase-celite catalyst as used in Example 1. 10 g of the catalyst were activated by mixture with 0.8 ml of distilled water and standing for 24 hours. The activated catalyst was then added to a solution of 100 g of the partially hydrolysed palm mid-fraction in 200 g of petroleum ether, BP 100° to 120° C., contained in a vessel with a headspace volume of approximately 900 ml in which the mixture was stirred for 6½ hours at 40° C. while the headspace gases were continuously circulated at a rate of 650 ml/minute, through a bed of 35 g molecular sieve type 4A. Reaction was then stopped, the composition of the reaction product determined and the fat removed. In Table II details of the composition are given, together with those of the original hydrolysed palm mid-fraction and others from comparative experiments, one using the dry catalyst without previous activation with water (Control A) and the other similarly activated catalyst but with no headspace gas circulation (Control B). The $A_W$ of the reaction mass, measured as described in Example 1, is given in Table III. For the dry catalyst run it remained between 0.09 and 0.04.

TABLE II

| | Wt % | | | | |
|---|---|---|---|---|---|
| | TG | 1,2 DG | 1,3 DG | MG | FFA |
| Partially hydrolysed palm mid-fraction | 76.8 | 13.1 | 1.0 | ND | 9.1 |
| Example 2 | 87.6 | 4.3 | 3.4 | ND | 4.7 |
| Control A | 65.3 | 17.9 | | 1.5 | 15.4 |
| Control B | 80.7 | 9.9 | 2.2 | ND | 7.2 |

With the activated catalyst extensive re-esterification is shown between the diglyceride and free fatty acid present, with the formation of triglyceride. With the dry catalyst only limited re-esterification is observed, with only a marginal increase in the amount of triglyceride present.

TABLE III

| | Water Activity | | | | | | |
| --- | --- | --- | --- | --- | --- | --- | --- |
| | Time (hours) | | | | | | |
| Example | 0.5 | 1.0 | 2.0 | 3.0 | 4.0 | 5.0 | 6.0 |
| 1 | 0.53 | 0.33 | 0.17 | 0.15 | 0.11 | 0.08 | 0.07 |
| 2 | 0.50 | 0.35 | 0.24 | — | 0.13 | — | 0.05 |

EXAMPLE 3

75 g of palm mid-fraction was interesterified with half its weight of stearic acid in solution in 140 ml of hexane to which was added 7.5 g of celite-(Aspergillus Niger lipase ex Amano Pharmaceuticals, Japan) (AP6) lipase enzyme catalyst, previously moistened with 10% its weight of water and stood overnight. The catalyst was prepared as described in Example 2 of British patent specification No. 1,577,933 and the enzyme had the same activity as already given above. The reaction mixture also contained 12 g of silica gel of 4 to 6 BSS mesh size that had been previously dried overnight at 105° C., and was stirred at 40° C. for 24 hours.

The course of the reaction followed by measuring the free fatty acid and stearate content in the triglycerides of samples recovered at intervals from the reaction mixture, the initial free fatty acid content being 1.17 Mmoles/g. The stearate content of the triglycerides was obtained by measuring the $C_{52}$ and $C_{54}$ contents of the triglycerides by GLC and, using a calibration curve for stearate content calculated from fatty acid methyl determination (FAME), determined on a separate interesterification reaction. The initial stearate content was 6.1%.

The analytical results are reported in Table IV, together with those from control experiments in one of which the catalyst was activated as before but no silica gel with added to the reaction mass (Control A). In the other (Control B) silica gel was moistened instead of the catalyst with the same amount of water as before. Water activities of silica gel samples were determined at 20° C. using a SINA Equihygroscope. In Example 3 initial water activity of the silica gel was 0.18; after reaction 0.28 and in Control B 0.35 and 0.34 respectively. Initial water activity of the catalyst in Example 3 was >0.95. Water solubility in the hexane solution of fat was 0.06% w/v, determined by a micro Karl Fischer method using an "Aquatest" apparatus.

TABLE IV

| | Example 3 | Control A | Control B |
| --- | --- | --- | --- |
| Stearate % in triglyceride after 500 min. | 19.0 | 20.6 | 10.7 |
| Stearate % in triglyceride after 24 hr. | 24.9 | 25.4 | 17.8 |
| Increase in FFA (Mmole/g) | | | |
| after 500 min | 0.14 | 0.22 | 0.13 |
| after 24 hr. | 0.16 | 0.27 | 0.15 |

Table IV shows that whereas in Example 3 virtually no more free fatty acid is generated than with the relatively inactive dry catalyst and substantially less than that using the activated catalyst without the silica gel to reduce the water activity as shown in the Table, almost as much stearate is produced in the Example as in the absence of $A_W$ control using the active catalyst.

EXAMPLE 4

A solution of 100 g of palm oil in 200 g of petroleum ether of BP 100° to 120° C. was stirred in a vessel with a headspace volume of approximately 900 ml, in contact with 10 g of a lipase-celite catalyst prepared as described in Example 1 above from R. japonicus lipase and a mixture of 1 ml of water and 0.5 ml of glycerine with which the catalyst had been activated by standing for 24 hours beforehand at 20° C. The mixture was maintained in the vessel at 40° C. while the headspace gases were continuously circulated at a rate of 650 ml/minute, through a bed of 35 g of molecular sieve type 4A. After 24 hours reaction was stopped, the solvent removed and the palm oil recovered and analysed. Further data appearing in Table V includes an analysis of product from the palm oil treated with active catalyst as in Example IV but with no headspace gas circulation.

TABLE V

| | TG | FFA | DG | MG |
| --- | --- | --- | --- | --- |
| Original palm oil | 92.3 | 2.7 | 5.0 | ND |
| Esterified palm oil | | | | |
| Example IV | 89.1 | 0.7 | 10.2 | ND |
| Control | 67.5 | 14.2 | 18.3 | 1.5 |

It will be seen that as a result of the reaction in Example 4 most of the free fatty acid present in the orginal oil is esterified during the reaction to yield predominantly additional diglyceride. No monoglycerides were detected either in the original palm oil or in the esterified product of Example 4, but in the Control a significant amount was produced.

EXAMPLE 5

This Example illustrates the effect of the invention on the preparation of oleyl ricinoleate. 0.25 g celite-lipase catalyst prepared as in Example 1 was hydrated by mixing with 0.025 ml water and standing overnight, to give an $A_W$ of greater than 0.95. 0.5 g oleyl alcohol and 0.56 g castor oil fatty acids were dissolved in hexane to give 5 ml solution. The hydrated lipase catalyst was added, immediately followed by 1.2 g silica gel M.F.C. grade ex Hopkin & Williams that had been dried overnight at 105° C. It may be calculated that this silica gel would take up water present on the catalyst so as to reduce $A_W$ below 0.6. This reaction mixture was stirred at 40° C. for 2 hrs, then a sample of the organic phase removed for analysis. For comparison, two similar reactions were carried out: omitting the silica gel (Control A); and using unhydrated catalyst and no silica gel (Control B).

The products were analysed. No ricinoleate polymers were detected in any sample. In addition to unchanged reactants the samples contained oleyl ricinoleates: 76.2% in the example and 41.2% (Control A) and 7.7% (Control B).

We claim:
1. A process for the preparation of rearranged esters susceptible to hydrolysis which comprises:
   (i) presoaking a catalyst comprising an esterase carried on a support with sufficient water to achieve a thermodynamic water activity of at least 0.5;
   (ii) subjecting a dispersion of reactants comprising a water-immiscible organic liquid and ester precur- sors to interesterification by contacting the presoaked activated catalyst with said dispersion in the presence of a means to remove water from the reaction dispersion, said ester precursors being selected from the group consisting of glycerides, partial glycerides, fatty acids, fatty alcohols, glycerol, and mixtures thereof;

(iii) substantially lowering the thermodynamic water activity of the reaction system after said catalyst is contacted with said dispersion to less than 0.4 and thereafter maintaining said thermodynamic water activity by said means to remove water; and (iv) recovering the rearranged esters from said dispersion.

2. The process according to claim 1, wherein the esterase comprises a lipase.

3. The process according to claim 1, wherein the ester precursors comprise glycerides.

4. The process according to claim 1, wherein said ester precursors are selected from the group consisting of partial glycerides, glycerol and mixtures thereof.

5. A process according to claim 1, wherein the ester precursor comprises free fatty acid.

6. A process according to claim 1, wherein the ester precursors comprise ricinoleic acid.

7. A process according to claim 1, wherein said esterase is carried on a support selected from the group consists of diatomaceous earth, hydroxylapatite, titanium dioxide, alumina and silica.

8. A process according to claim 7, wherein the support comprises diatomaceous earth.

9. A process according to claim 1, wherein the esterose is activated with from 1.1 to 30% water by weight of the catalyst, including the weight of any catalyst support.

10. A process according to claim 1, wherein the water immiscible organic liquid comprises a hydrocarbon.

11. A process according to claim 1, wherein said means to remove water comprises a molecular sieve, silica gel, alumina, magnesium sulfate or calcium chloride.

12. A process according to claim 1, wherein said means to remove water is in contact with the vapor phase of the dispersion.

13. A process according to claim 1 wherein steps (ii) and (iii) are carried out at a temperature from 10° to 70° C.

14. A process according to claim 1, wherein the esterase comprises *Aspergillus niger* lipase.

15. A process according to claim 1, wherein the esterase comprises *Rhizopus japonicus* lipase and the water activity is lowered to less than 0.3

16. A process according to claim 1, wherein the esterase comprises a lipase, the ester precursor comprises free fatty acid, and the water immiscible organic liquid comprises a hydrocarbon.

17. A process for the preparation of esters susceptible to hydrolysis which comprises:

(i) presoaking a catalyst comprising an esterase carried on a support with sufficient water to achieve a thermodynamic water activity of at least 0.5;

(ii) subjecting a dispersion of reactants comprising ester precursors to interesterification by contacting the presoaked activated catalyst with said dispersion in the presence of a means to remove water from the reaction dispersion, said ester precursors being selected from monocarboxylic acids and monohydric alcohols;

(iii) substantially lowering the thermodynamic water activity of the reaction system after said catalyst is contacted with said dispersion to less than 0.4 and thereafter maintaining said thermodynamic water activity by said means to remove water; and (iv) recovering the esters from said dispersion.

* * * * *